United States Patent [19]

Buschmann et al.

[11] Patent Number: 5,728,885
[45] Date of Patent: Mar. 17, 1998

[54] METHOD OF PREPARING THE ENANTIOMERS OF O-DIMETHYLTRAMADOL

[75] Inventors: Helmut Buschmann; Werner Winter, both of Aachen; Ivars Graudums, Stolberg; Peter Jansen, deceased, late of Eschweiler, by Ursula Jansen, Heiress; Wolfgang Werner Alfred Strassburger, Wuerselen; Elmar Josef Friederichs, Stolberg, all of Germany

[73] Assignee: Gruenenthal GmbH, Aachen, Germany

[21] Appl. No.: 784,078

[22] Filed: Jan. 17, 1997

[30] Foreign Application Priority Data

Jan. 19, 1996 [DE] Germany ............... 196 01 744.0

[51] Int. Cl.$^6$ .................................................. C07C 209/88
[52] U.S. Cl. .......................... 564/304; 564/302; 564/443
[58] Field of Search ........................... 564/302, 304, 564/443; 514/646

[56] References Cited

U.S. PATENT DOCUMENTS

| | | | |
|---|---|---|---|
| 3,652,589 | 3/1972 | Flick et al. ............... | 548/578 |
| 5,468,744 | 11/1995 | Raffa et al. ............... | 514/282 |

FOREIGN PATENT DOCUMENTS

| | | |
|---|---|---|
| 534628 | 3/1993 | European Pat. Off. . |
| 1084006 | 9/1967 | United Kingdom . |
| WO 93/04675 | 3/1993 | WIPO . |

OTHER PUBLICATIONS

Jacques et al., *Enantiomers, Racemates and Resolutions,*, 1991, Krieger Publishing Company, Malabar, Florida, pp. 259–261 and pp. 387–388.

Winterfeldt, "Applications of Diisobutylaluminium Hydryde (DIBAH) and Triisobutylaluminium (TIBA) as Reducing Agents in Organic Synthesis", *Synthesis*, Oct. 1975, pp. 617–630.

Sevcik et al., "Effects of the Central Analgesic Tramadol and Its Main Metabolite, O–desmethyltramadol, on Rate Locus Coeruleus Neurons", *Chemical Abstracts*, vol. 119, No. 25, Dec. 20, 1993, Abstract No. 262330.

Dayer et al., "The Pharmacology of Tramadol", *Chemical Abstracts*, vol. 121, No. 19, Nov. 7, 1994, Abstract No. 220754.

Flick et al., "Untersuchungen zur chemischen Struktur und analgetischen Wirkung von phenylsubstitutierten Aminomethylcyclohexanolen", *Arzneimittel Forschung—Drug Research*, vol. 28, No. 1a, Jan. 1, 1978, pp. 107–113.

Frankus et al., "Uber die Isomerentrennung, Strukturaufklarung und pharmakologische Charakterisierung von 1–(m–Methoxyphenyl)–2–(dimethylaminomethyl)–cyclohexan–1–ol", *Arzneimittel Forschung—Drug Research*, vol. 28, No. 1A, (1978), pp. 114–121.

*Primary Examiner*—Richard L. Raymond
*Attorney, Agent, or Firm*—Evenson, McKeown, Edwards & Lenahan P.L.L.C.

[57] ABSTRACT

A method of preparing the enantiomers of O-demethyltramadol and the use of the enantiomers as pain-killing drugs are described.

8 Claims, No Drawings

METHOD OF PREPARING THE ENANTIOMERS OF O-DIMETHYLTRAMADOL

This invention relates to a method of preparing the enantiomers of O-demethyltramadol and to their use as pain-killing drugs.

Opioids have been used for many years as analgesics for the treatment of pain, even though they give rise to a series of side effects, for example addiction and dependency, respiratory depression, gastrointestinal inhibition effects and obstipation. They can therefore only be given over an extended period of time or in higher doses subject to individual regulatory measures such as special prescription regulations (Goodman, Gilman, The Pharmaceutical Basis of Therapeutics, Pergamon Press, New York, 1990). Tramadol hydrochloride—(1RS, 2RS)-2-dimethylaminomethyl-1-(3-methoxy-phenyl)-cyclohexanol hydrochloride—assumes a special position amongst centrally acting analgesics, since this active ingredient acts as a strong inhibitor of pain without the side effects which are known for opioids (J. Pharmacol. Exptl. Ther. 267, 331 (1993)). Tramadol is a racemate and consists of equal amounts of (+)- and (−)-enantiomers. In vivo, this active ingredient forms the metabolite O-demethyltramadol, which likewise exists as a mixture of enantiomers. Investigations have shown that both the two enantiomers of tramadol and the two enantiomers of the tramadol metabolite are involved in the analgesic effect (J. Pharmacol. Exptl. Ther. 260, 275 (1992); Arzneim.-Forschung 38, 877 (1988)).

The preparation of O-demethyltramadol as a racemate or in the form of the enantiomers is known from EP 534 628 and WO 93/04675. However, O-demethyltramadol can only be obtained in unsatisfactory yields by this method, which is carried out using a strong base such as sodium or potassium hydride in the presence of thiophenol and diethylene glycol. The underlying object of the present invention therefore consisted of developing a method with which O-demethyltramadol can be prepared in high yields.

It has been found that O-demethyltramadol can be prepared in the form of its pure enantiomers in high yield by using L-(+)-tartaric acid for separating the racemate of tramadol and subsequent methyl ether cleavage with diisobutylaluminium hydride (DIBAH).

Accordingly, the present invention relates to a method of preparing the enantiomers of O-demethyltramadol which is characterised in that a racemic tramadol salt is converted into the base, the (−)-tramadol enantiomer is separated by precipitation with L-(+)-tartaric acid and after releasing the base is converted into the (−)-enantiomer of O-demethyltramadol with DIBAH, and the (+)-enantiomer of O-demethyltramadol is prepared from the mother liquor from tartaric acid precipitation by releasing the tramadol base and reaction with DIBAH.

Racemic tramadol hydrochloride is particularly suitable as a starting material for the method according to the invention. This is converted into the racemic tramadol base in an aqueous solution by the addition of alkali hydroxides, preferably sodium hydroxide, and extraction with an organic solvent, for example dichloromethane and/or diethyl ether. The base obtained is subsequently treated with L-(+)-tartaric acid, preferably in the presence of an organic solvent, most preferably in the presence of an aliphatic $C_{1-5}$ alcohol. The tartrate of the (−)-tramadol enantiomer which forms is separated, preferably by crystallisation, from the tartrate of the (+)-tramadol enantiomer formed, and is converted into the (−)-enantiomer of O-demethyltramadol with DIBAH after releasing the tramadol base under the aforementioned conditions. The methyl ether cleavage with DIBAH is usually conducted in an aromatic hydrocarbon, for example toluene, at a temperature between 60° and 130° C.

The (+)-tramadol enantiomer which is soluble in the mother liquor in the form of the tartrate salt is converted into the (+)-enantiomer of O-demethyltramadol by releasing the tramadol base under the aforementioned conditions and subsequent reaction with DIBAH under the aforementioned conditions.

The enantiomers of O-demethyltramadol which are obtained may be isolated as bases or as salts, particularly as hydrochlorides. The hydrochlorides can be obtained under the same conditions as the hydrochlorides of tramadol.

Before the reaction with DIBAH, it is advantageous to convert the base released from the tartrate of the respective tramadol enantiomer into a tramadol salt which is different from the tartrate, preferably into a hydrochloride, and to release the tramadol base again from the latter under the aforementioned conditions.

Conversion of the tramadol base into the hydrochloride can be effected with concentrated hydrochloric acid or gaseous hydrogen chloride in an organic solvent, for example acetone, dioxane, diethyl ether and/or diisopropyl ether, or with trimethylchlorosilane/water in a solvent, for example 2-butanone.

Using the method according to the invention, the enantiomers of O-demethyltramadol can be prepared economically, in an environmentally friendly manner, and in high yields. Only an enantiomeric form of tartaric acid, namely the inexpensive L-(+)-tartaric acid, is necessary for separating the racemate of a tramadol salt. With L-(+)-tartaric acid the tramadol enantiomers can be obtained in a yield of more than 85% with respect to the racemate used, and with an enantiomer purity greater than 98%. The mother liquor can be recycled to the racemate separation process after releasing the tramadol base. The methyl ether cleavage gives the enantiomers of O-demethyltramadol in greater than 95% yield.

The use of O-demethyltramadol in combination with codeine, oxycodone, hydrocodone or acetaminophen for the treatment of pain situations is described in EP 534 628 and WO 93/04675. It has now been found that even O-demethyltramadol on its own or in combination with tramadol possesses a high analgesic effect.

Therefore, the present invention also relates to the use of O-demethyltramadol as a base and/or salt in the form of a racemate or of an enantiomer, on its own or in combination with tramadol as a base and/or salt in the form of a racemate or of an enantiomer, as an analgesic active ingredient in a drug.

The (+)-enantiomer of O-demethyltramadol is preferably used.

In addition to the base and/or at least one salt of O-demethyltramadol, on its own or in combination with tramadol base and/or at least one tramadol salt, the analgesics according to the invention contain support materials, fillers, solvents, diluents, colorants and/or binders. The selection of these auxiliary materials and of the amounts thereof to be used depends upon whether the drug is to be applied orally, intravenously, buccally, intraperitoneally, intradermally, intramuscularly, intranasally or locally, for example to the skin, to the mucous membranes or to the eyes. Preparations in the form of tablets, dragees, capsules, granules, drops, juices and syrups are suitable for oral application. Solutions, suspensions, readily reconstitutable dry preparations and sprays are suitable for parenteral or topical application and for application by inhalation. The compounds which are to be used according to the invention as a deposit in dissolved form or in a patch, optionally with the addition of agents which promote dermal penetration, are suitable percutaneous forms of application. Forms of preparations which can be applied orally or percutaneously are capable of releasing the compounds to be used according to the invention in a delayed manner.

The amount of active ingredient to be administered to the patient varies depending on the weight of the patient, on the type of application, on the indication and on the degree of severity of the illness. 5 to 500 mg/kg of at least one of the aforementioned compounds is usually administered.

EXAMPLES

Example 1

(−)-(1S, 2S)-2-dimethylaminomethyl-1-(3-methoxy-phenyl)-cyclohexanol hydrochloride (−1)

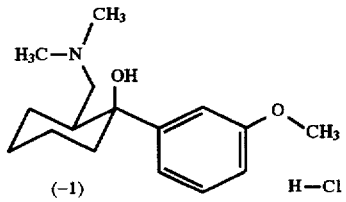

1st step: release of the racemic base 3 kg (10 mole) (1RS, 2RS)-2-dimethylaminomethyl-1-(3-methoxy-phenyl)-cyclohexanol hydrochloride (1) were suspended in 4800 ml water and treated with 1.6 kg crushed ice. 1300 ml of 36–38% (technical) caustic soda solution were added drop-wise with stirring. The mixture was subsequently extracted with 7000 ml dichloromethane, and was extracted with a further 2000 ml dichloromethane after phase separation. The combined organic phases were dried over sodium sulphate. After removing the solvent by distillation, 2630 g (99% theoretical) of (1RS, 2RS)-2-dimethylaminomethyl-1-(3-methoxy-phenyl)-cyclohexanol were obtained as a syrup.

2nd stage: precipitation with L-(+)-tartaric acid 2630 g (10 mole) of the base from the first step were dissolved in 2400 ml ethanol and treated with a solution consisting of 1500 g (10 mole) L-(+)-tartaric acid and 11,200 ml ethanol. The mixture was stirred for two hours at room temperature and allowed to stand for 24 hours at 4° C. to effect crystallisation. The precipitated crystals were filtered off under suction and washed with 6400 ml ethanol at 4° C. After drying the crystalline material at room temperature in vacuum (60 mbar), 2050 g (49% with respect to the total amount of racemic base used) of (1S, 2S)-2-dimethylaminomethyl- 1-(3-methoxy-phenyl)-cyclohexanol L-(+)-tartrate with a melting point of 173°–175° C. were obtained (specific rotation: $[\alpha]^{RT}_D = -12.2°$ (c=1.01; methanol)).

3rd step: release of the base from the L-(+)-tartaric acid salt 2050 g (4.95 mole) (1S, 2S)-2-dimethylaminomethyl-1-(3-methoxy-phenyl)-cyclohexanol L-(+)-tartrate from step 2 were dissolved in 4000 ml water and treated with 900 g crushed ice. 1000 ml of 36–38 % (technical) caustic soda solution were added drop-wise with stirring. The mixture was subsequently extracted with 2500 ml dichloromethane, and was extracted with a further 500 ml dichloromethane after phase separation. The combined organic phases were dried over sodium sulphate. After removing the solvent by distillation, 1280 g (99% theoretical) of (1S, 2S)-2-dimethylaminomethyl-1-(3-methoxy-phenyl)-cyclohexanol were obtained as a syrup.

4th step: conversion of (1S, 2S)-2-dimethylaminomethyl-1-(3-methoxy-phenyl)-cyclohexanol into the hydrochloride (−1)

1280 g (4.86 mole) of the base obtained from step 3 were dissolved in 16 l 2-butanone and were treated with 88 ml (4.9 mole) water and 621 ml (532 g; 4.9 mole) trimethylchlorosilane with stirring. The mixture was stirred for 3 hours at room temperature and allowed to stand for 24 hours at 4° C. to effect crystallisation. The precipitated solid was filtered off under suction, washed with 5000 ml 2-butanone at 4 ° C. and dried to constant weight at 90° C. under vacuum (60 mbar). 1390 g (95% theoretical with respect to the base from step 3 which was used, and 92% with respect to the enantiomer content of the racemate from step 1 which was used) of hydrochloride (−1) were obtained as colourless crystals.

Melting point: 172°–173 ° C.

Specific rotation: $[\alpha]^{RT}_D = -29.6°$ (c=1.00; methanol).

5th step: conversion of hydrochloride (−1) into (−)-(1S, 2S)-3-(2-dimethylaminomethyl-1-hydroxy-cyclohexyl)-phenol hydrochloride

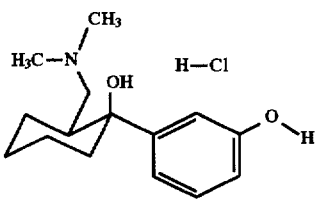

The base was released from hydrochloride (−1) with dichloromethane/sodium hydroxide solution under the conditions given in the 1st step. After drying the solution, the dichloromethane was distilled off under vacuum. 208.1 g (0.79 mole) of the base obtained, dissolved in 360 ml toluene, were added drop-wise at room temperature to 1.6 l of a 20% solution of diisobutylaluminium hydride (1.58 mole) in toluene. The mixture was then heated for 11 hours under reflux, and after cooling to room temperature it was further cooled to about 0° C. with ice/common salt. 450 ml ethanol were then added drop-wise in such a way that the internal temperature did not exceed 15° C. After the addition was complete, the mixture was stirred for a further 15 minutes and diluted with 1000 ml toluene. 450 ml of an ethanol/water mixture (1:1) were added drop-wise whilst cooling the mixture in ice/common salt; after the addition was complete, the mixture was stirred for one hour at room temperature. The precipitated aluminium hydroxide was filtered off under suction and stirred with five parts by volume of ethyl acetate at 60° C. for subsequent extraction. After filtering off under suction again, the combined organic phases were dried over sodium sulphate and concentrated at 60° C. in a rotary evaporator. 193 g (98 % theoretical) of base were obtained; the base crystallised out as a solid with a melting point of 139°–142° C.

The crude product obtained was dissolved in 1.93 l acetone and treated with 65 ml concentrated hydrochloric acid. After crystallisation had commenced, the product was stirred for one hour whilst being cooled in an ice bath before the precipitate was filtered off under suction. The precipitate was washed twice with acetone and with diethyl ether, and the crystalline material was subsequently dried to constant weight at 70° C. under the vacuum from an oil pump. 216.8 g (96 % theoretical) of colourless crystals were obtained.

Melting point: 247°–248° C. (decomposition)
Specific rotation: $[\alpha]^{RT}_D = -35.2°$ (c=1.00; methanol).

Example 2

(+)-(1R, 2R)-2-dimethylaminomethyl-1-(3-methoxy-phenyl)-cyclohexanol hydrochloride (+1)

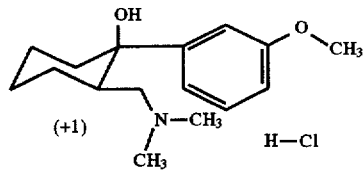

1st step: release of the base from the mother liquor from L-(+)-tartaric acid precipitation The ethanolic mother liquor and the washing phase from L-(+)-tartaric acid precipitation (Example 1, 2nd step) were combined. After removing the solvent by distillation, the residue (2080 g) was dissolved in 2500 ml water and treated with 900 g crushed ice. 1000 ml of 36–38 % (technical) caustic soda solution were added drop-wise with stirring. The mixture was subsequently extracted with 2700 ml dichloromethane, and was extracted with a further 600 ml dichloromethane after phase separation. The combined organic phases were dried over sodium sulphate. After removing the solvent by distillation, 1340 g (99% theoretical) of (1R, 2R)-2-dimethylaminomethyl-1-(3-methoxy-phenyl)-cyclohexanol were obtained as a syrup.

2nd step: conversion of (1R, 2R)-2-dimethylaminomethyl-1-(3-methoxy-phenyl)-cyclohexanol into the hydrochloride (+1)

1340 g (5.09 mole) of the base obtained from step 1 were dissolved in 17.5 l 2-butanone and treated with 105 ml (5.8 mole) water and with 670 ml (573 g; 5.3 mole) trimethylchlorosilane with stirring. The mixture was stirred for 3 hours at room temperature and allowed to stand for 24 hours at this temperature to effect crystallisation. The precipitated solid was filtered off under suction, washed with 5000 ml 2-butanone and dried to constant weight at 90° C. under vacuum (60 mbar). 1350 g (88% theoretical with respect to the base from step 1 which was used, and 89% with respect to the enantiomer content of the racemate from Example 1, step 1 which was used) of hydrochloride (+1) were obtained as colourless crystals.

Melting point: 171°–172° C.
Specific rotation: $[\alpha]^{RT}_D = +29.6°$ (c=1.00; methanol).

3rd step: conversion of hydrochloride (+1) into (+)-(1R, 2R)-3-(2-dimethyl-aminomethyl-1-hydroxy-cyclohexyl)-phenol hydrochloride

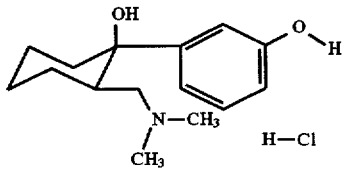

The (+)-enantiomer of O-demethyltramadol was obtained as the hydrochloride in 96% yield starting from hydrochloride (+1), under the conditions given in Example 1, 5th step.

Melting point: 247°–248° C. (decomposition)
Specific rotation: $[\alpha]^{RT}_D = +35.4°$ (c=1.00; methanol).

Pharmacological Investigations

Testing for analgesia using the writhing test on mice

Testing for analgesic effectiveness was performed using the phenylquinone-induced writhing test on mice (modified according to I. C. Hendershot, J. Forsaith, J. Pharmacol. Exp. Ther. 125, 237–240 (1959)). Male NMRI mice with a weight of 25–30 g were used for this purpose. For each dose of substance, groups of 10 animals received, 10 minutes after the intravenous administration of the compounds to be used according to the invention, 0.3 ml per mouse of an 0.02% aqueous solution of phenylquinone (phenylbenzoquinone: manufactured by Sigma, Deisenhofen; solution prepared with the addition of 5 % ethanol and kept on a water bath at 45° C.) administered intraperitoneally. The animals were placed individually in observation cages, and the number of pain-induced stretching movements (so-called writhing reactions=straightening of the body with stretching of the rear extremities) 5–20 minutes after the administration of phenylquinone was counted by means of a push-button counter. The $ED_{50}$ values were calculated with a 95% confidence limit by means of regression analysis (evaluation program supplied by Martens EDV Service, Eckental) from the dose-dependent decrease in the writhing reactions, by comparison with control groups which were tested in parallel and which were treated with phenylquinone only.

Testing for analgesia using the tail flick test on rats

The analgesic effectiveness of the compounds to be used according to the invention was investigated in the thermal radiation (tail flick) test on rats using the method of D'Amour and Smith (J. Pharm. Exp. Ther. 72, 74–79 (1941). Female Sprague Dawley rats with a weight of 120–160 g were used for this purpose. The animals were placed individually in test cages and the bases of their tails were exposed to the focused thermal radiation from an electric lamp (Rhema Analgesiemeter for rats). The lamp intensity was adjusted so that the time from switching on the lamp until the sudden twitching away of the tail (latency of pain) was 3–6 seconds for untreated animals. Before the administration of the compounds to be used according to the invention, the animals were tested twice within five minutes and the average value of these measurements was calculated as the pre-test average. The pain measurement was made 20, 40 and 60 minutes after intravenous administration. When the latency of pain increased, the maximum time of exposure was restricted to 12 seconds and an increase in the latent period to >150 % of the pre-test average value was assessed as an analgesic effect. In order to determine the dosage-dependency, the compounds were administered in doses increasing logarithmically by a factor of 3–5, which included the threshold and the maximum effective dose each time. The $ED_{50}$ values were determined from the number of analgesic animals by the method of Litchfield and Wilcoxon (J. Pharm. Exp. Ther. 96, 99–113, (1949)). The $ED_{50}$ was calculated at the effective maximum 20 minutes after intravenous administration of the substance.

The enantiomers of O-demethyltramadol to be used according to the invention exhibited a pronounced analgesic effect in the writhing test on mice and in the tail flick test on rats. The results are summarised in the following Table.

TABLE

Testing for analgesia using the writhing test on mice and the tail flick test on rats

| Compound | ED$_{50}$ (mg/kg, intravenous) in the writhing test | ED$_{50}$ (mg/kg, intravenous) in the tail flick test |
| --- | --- | --- |
| (+)-enantiomer of O-demethyltramadol hydrochloride | 0.489 | 1.01 |
| (−)-enantiomer of O-demethyltramadol hydrochloride | 6.60 | >10.0 |
| For comparison: racemic tramadol hydrochloride | 3.59 | 6.47 |

We claim:

1. A method of preparing enantiomers of O-demethyltramadol, comprising the steps of:
   providing a racemic solution of (−)- and (+)-tramadol enantiomers in free base form;
   precipitating (−)-tramadol enantiomer with L-(+)-tartaric acid and separating precipitate from mother liquor;
   releasing the (−)-tramadol enantiomer from the precipitate as a (−)-tramadol enantiomer free base;
   reacting the (−)-tramadol enantiomer free base with diisobutylaluminium hydride to convert it into (−)-enantiomer of O-demethyltramadol;
   releasing the (+)-tramadol enantiomer from the mother liquor as a (+)-tramadol enantiomer free base, and
   reacting the (+)-tramadol enantiomer free base with diisobutylaluminium hydride to convert it into (+)-enantiomer of O-demethyltramadol.

2. A method according to claim 1, wherein said racemic solution is provided by converting a racemic tramadol salt into a corresponding base.

3. A method according to claim 2, wherein said racemic tramadol salt is racemic tramadol hydrochloride.

4. A method according to claim 1, wherein said precipitating step is carried out in an organic solvent.

5. A method according to claim 4, wherein said organic solvent comprises an aliphatic $C_{1-5}$ alcohol.

6. A method according to claim 1, wherein said precipitating step is effected by crystallization of (−)-tramadol L-(+)-tartrate.

7. A method according to claim 1, further comprising an intermediate step of converting released tramadol enantiomer free base into a salt other than a tartrate, and then releasing the respective enantiomer in free base form from the other salt prior to reacting the free base with diisobutylaluminium hydride.

8. A method according to claim 7, wherein the released tramadol enantiomer free base is converted into a hydrochloride salt.

* * * * *